US011413401B2

(12) United States Patent
Tarlochan et al.

(10) Patent No.: US 11,413,401 B2
(45) Date of Patent: Aug. 16, 2022

(54) PLUNGER RESTRICTED SAFETY SYRINGE

(71) Applicant: QATAR UNIVERSITY, Doha (QA)

(72) Inventors: Faris Tarlochan, Lusail (QA); Sami Alkhatib, Barwa (QA)

(73) Assignee: QATAR UNIVERSITY, Doha (QA)

( * ) Notice: Subject to any disclaimer, the term of this patent is extended or adjusted under 35 U.S.C. 154(b) by 145 days.

(21) Appl. No.: 16/295,462

(22) Filed: Mar. 7, 2019

(65) Prior Publication Data

US 2020/0254193 A1 Aug. 13, 2020

Related U.S. Application Data

(60) Provisional application No. 62/805,137, filed on Feb. 13, 2019.

(51) Int. Cl.
*A61M 5/32* (2006.01)
*A61M 5/50* (2006.01)
*A61M 5/315* (2006.01)
*A61M 5/31* (2006.01)

(52) U.S. Cl.
CPC ........ *A61M 5/3221* (2013.01); *A61M 5/3129* (2013.01); *A61M 5/31511* (2013.01); *A61M 5/50* (2013.01); *A61M 2005/323* (2013.01)

(58) Field of Classification Search
CPC .. A61M 5/322; A61M 5/3221; A61M 5/3129; A61M 5/50; A61M 5/31511; A61M 2005/323; A61M 2005/3231
See application file for complete search history.

(56) References Cited

U.S. PATENT DOCUMENTS

| | | | | |
|---|---|---|---|---|
| 3,028,862 | A | * | 4/1962 | Prater, Jr. ........... A61M 5/31511 604/222 |
| 4,354,507 | A | * | 10/1982 | Raitto ................. A61M 5/3129 600/576 |
| 4,900,311 | A | | 2/1990 | Stern et al. |
| 5,007,903 | A | * | 4/1991 | Ellard ................. A61M 5/3129 604/110 |
| 5,222,944 | A | | 6/1993 | Harris |
| 5,336,198 | A | | 8/1994 | Silver et al. |
| 6,287,279 | B1 | | 9/2001 | Siekmann |

(Continued)

FOREIGN PATENT DOCUMENTS

CA 2050440 A1 8/1991

OTHER PUBLICATIONS

Changzhou Medical Appliances General Factor Co., Ltd., "Safety Syirnge (Needle retractable and (plunger lock)," published at URL < https://medical88.en.made-in-china.com/productimage/SbFmWwTYEjkJ-2f1jOOutTUzAaCRgql/China-Safety-Syirnge-Needle-retractable-and-plunger-lock-.html > visited Feb. 10, 2019, 4 pages.

(Continued)

*Primary Examiner* — James D Ponton
(74) *Attorney, Agent, or Firm* — Squire Patton Boggs (US) LLP

(57) ABSTRACT

To prevent accidental needle stick injuries, a syringe has a plunger configured to pull the syringe needle into the syringe barrel after clinical use. The syringe has an additional safety feature that restricts subsequent movement of the plunger. After the needle is pulled entirely into the barrel, movement of the plunger is restricted by a notch on the barrel to prevent the needle tip from being pushed accidentally through the barrel wall.

10 Claims, 5 Drawing Sheets

(56) References Cited

U.S. PATENT DOCUMENTS

| | | |
|---|---|---|
| 6,342,045 B1 | 1/2002 | Somers |
| 6,702,786 B2 | 3/2004 | Olovson |
| 9,302,077 B2 | 4/2016 | Domonkos et al. |
| 2003/0040713 A1 | 2/2003 | Wang et al. |
| 2003/0139706 A1* | 7/2003 | Gray ............... A61M 5/315 604/199 |
| 2014/0088500 A1* | 3/2014 | Li ................. A61M 5/322 604/110 |
| 2017/0239425 A1* | 8/2017 | Castanon ......... A61M 5/3221 |

OTHER PUBLICATIONS

Guangdong Intmed Medical Appliance Co., Ltd., "Automatic syringe retractable syringes safety luer lock CE, approval FDA, ISO," published at URL<https://www.alibaba.com/product-detail/automatic-syringe-retractable-syringes-safety-luer_1845456752.html > visited Feb. 10, 2019, 5 pages.

Retractable Technologies, "Retractable Tech VanishPoint Syringes," published at URL<https://www.medexsupply.com/iv-administration-iv-admin-supplies-iv-syringes-retractable-tech-vanishpoint-syringes-10cc-20g-x-1-5-100-bx-x_pid-89928.html?pid=89928&gclid=EAlalQobChMl6uDw546M4AlVyJCfChOCxgbsEAkYBCABEglbGfD_BwE > visited Feb. 10, 2019, 3 pages.

* cited by examiner

PLUNGER RESTRICTED SAFETY SYRINGE

CROSS-REFERENCE TO RELATED APPLICATION

This application claims the benefit of Provisional Application No. 62/805,137, filed Feb. 13, 2019, which is hereby incorporated by reference.

FIELD

This disclosure relates generally to a syringe and, more particularly, to a syringe with a safety feature to prevent accidental needle stick injuries.

BACKGROUND

Conventionally, a cap covers the needle of a syringe. The cap is removed before drawing a patient's blood or injecting a substance into the patient. Thereafter, the cap is placed back over the needle to prevent an accidental needle stick injury. However, a needle stick injury may occur before the cap is placed back on the needle, or it may occur if the cap falls off inadvertently. Accidental needle stick (stab) injuries pose serious health risks, such as infection by HIV, hepatitis or other virus. Accordingly, there is a continuing need for safety features to reduce needle stick injuries.

SUMMARY

Briefly and in general terms, the present invention is directed to syringe.

In aspects, a syringe comprises a barrel, a needle, and a plunger. The barrel comprises a barrel forward segment, a barrel rear segment, a barrel medial segment between the barrel forward segment and the barrel rear segment. The barrel interior surface extends from the barrel rear segment to the barrel forward segment. The barrel rear segment has a neck section adjacent the barrel medial segment, a rear section, and a lock section between the neck section and the rear section. The barrel interior surface has a first internal diameter at the lock section and a second internal diameter at the neck section. The second internal diameter is less than the first internal diameter. The needle is configured for attachment on the barrel forward segment. The plunger comprises a first catch. The plunger is sized to pass through an opening formed through the rear section of the barrel rear segment. The plunger is configured to be pushed from a first position at which the first catch is in barrel medial segment, then to a second position at which the first catch is in the barrel forward segment, and then pulled to a third position at which the first catch is in the lock section of the barrel rear segment.

The features and advantages of the invention will be more readily understood from the following detailed description which should be read in conjunction with the accompanying drawings.

DETAILED DESCRIPTION

Figure 1A:
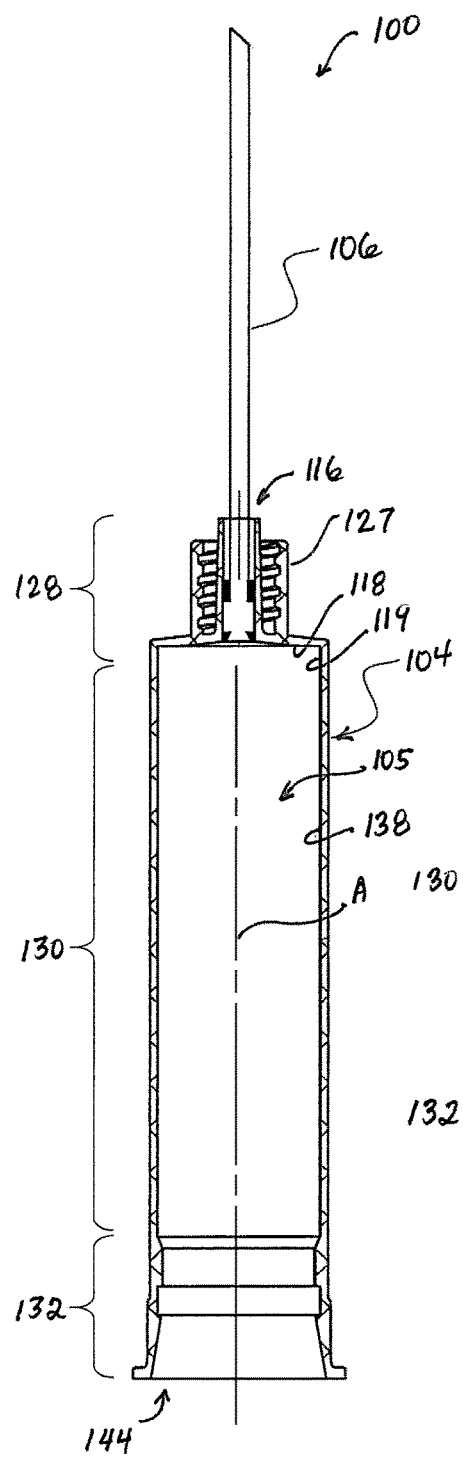
FIG. 1A is a cross-section view of a barrel and a needle of a syringe.

Referring now in more detail to the drawings for purposes of illustrating non-limiting examples, wherein like reference numerals designate corresponding or like elements among the several views, there is shown in FIGS. 1A-4 example syringe 100 having a safety feature for reducing needle stick injuries. Syringe 100 comprises plunger 102 (FIG. 2), barrel 104, and hollow needle 106. Barrel 104 is a hollow cylinder with barrel cavity 105.

Figure 1B:
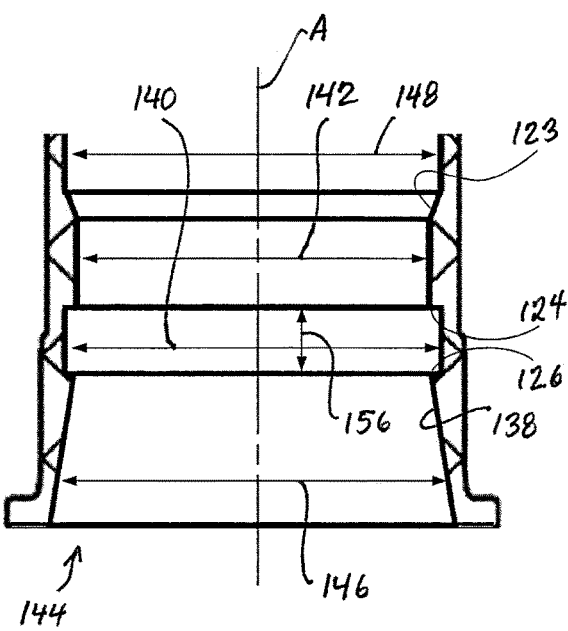
FIG. 1B is an enlarged cross-section view of a rear segment of the barrel.

FIG. 1A shows syringe 100 with plunger 102 omitted so that certain features of barrel 104 may be seen clearly. FIG. 1A may correspond to the state of syringe 100 before plunger 102 is installed in barrel 104 during manufacturing and industrial assembly. FIG. 1B shows an enlarged view of the rear segment of barrel 104.

Figure 2:
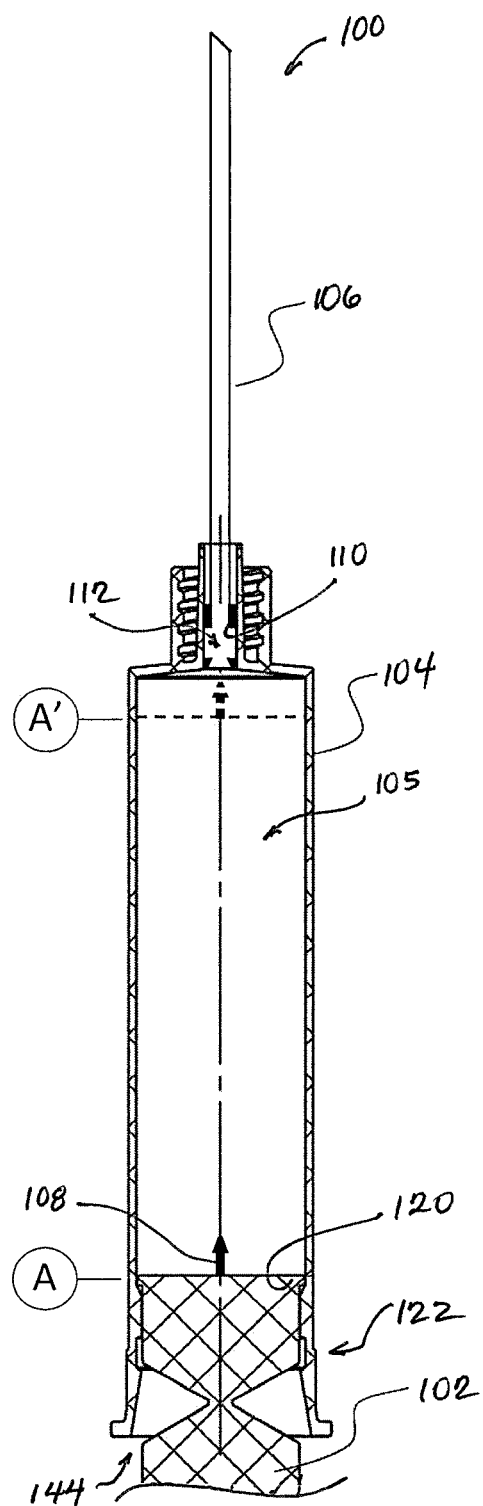
FIG. 2 is a cross-section view of the syringe showing a plunger in a first position in the barrel, at which position a first catch of the plunger is not locked within a notch formed of the barrel.
Figure 3:
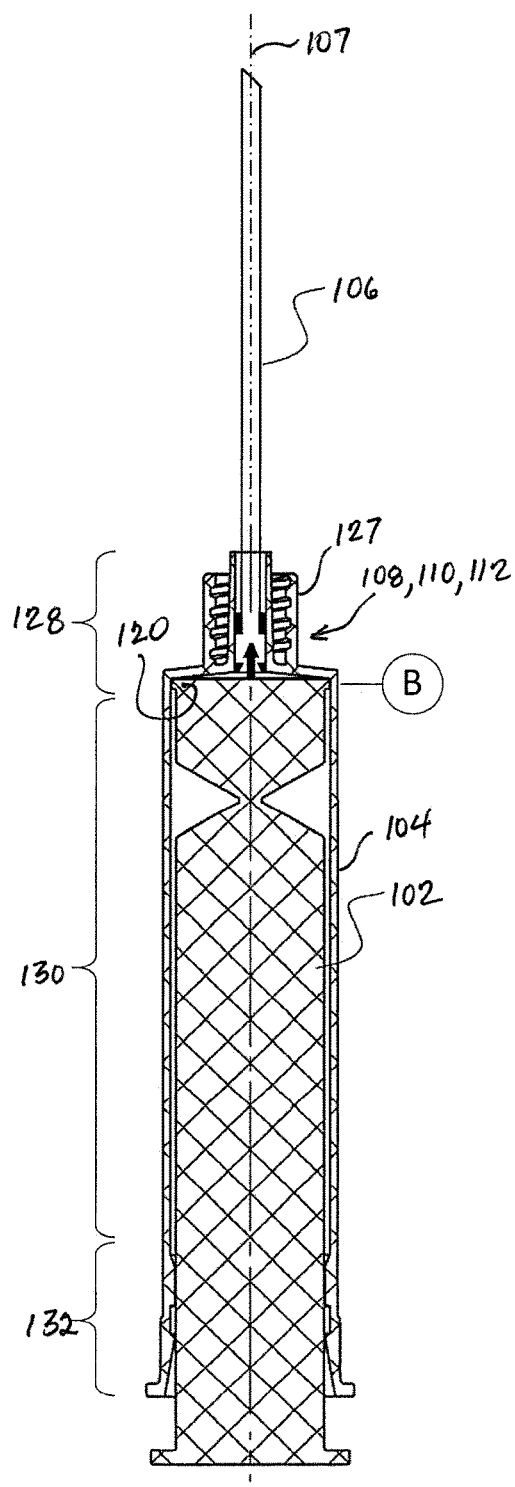
FIG. 3 is a cross-section view of the syringe showing the plunger in a second position in the barrel, at which position a second catch of the plunger attaches to a needle base of the needle.
Figure 4:
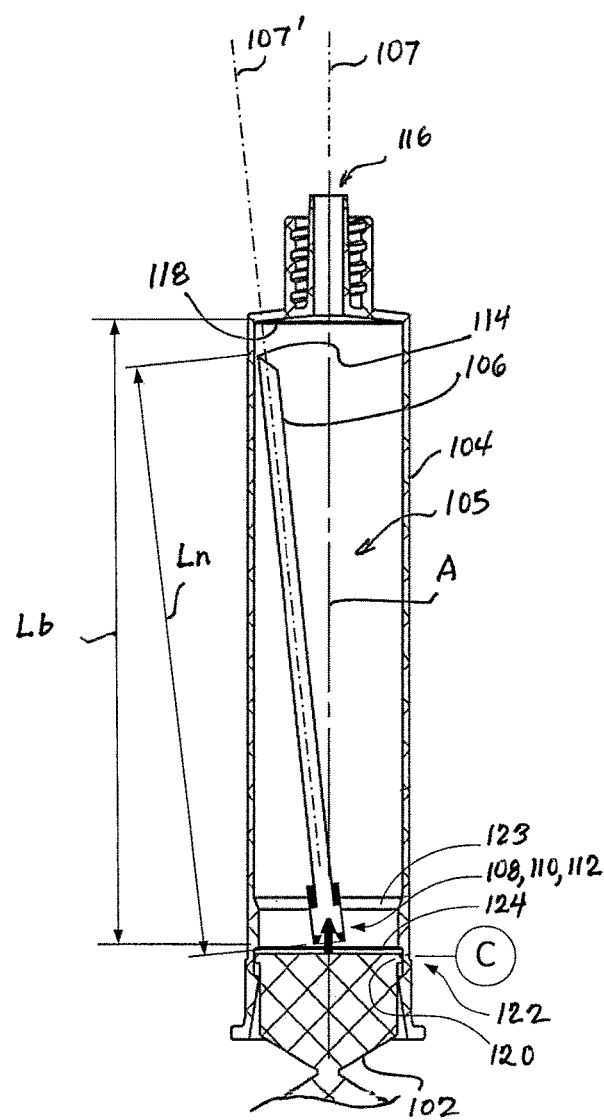
FIG. 4 is a cross-section view of the syringe showing the plunger in a third position in the barrel, at which position the second catch of the plunger is locked within the notch of the barrel.

FIGS. 2-4 show syringe 100 with plunger 102 at different positions within barrel 104. For example, FIGS. 2-4 may correspond to various states of syringe 100 during clinical use. The top portion of plunger 102 may be moved to and from positions A and A' (FIG. 2) in order to draw fluid into needle 106 and barrel cavity 105 and to expel the fluid out of barrel cavity 105 and needle 106. In FIG. 2, the top portion of plunger 102 is illustrated in broken lines at position A'. At position A, the top portion of plunger 102 rests on a bevel forming a slight constriction in barrel 104, which provides the user with tactile feedback so that the user does not inadvertently pull plunger 102 into a locked position, as will be discussed in detail further below.

As shown in FIG. 2, plunger 102 comprises second catch 108. Needle 106 comprises needle base 110, which has needle base cavity 112.

FIG. 3 shows syringe 100 after the user has completed an injection procedure. The top portion of plunger 102 has been pushed all the way into barrel 104 to position B, which results in second catch 108 entering cavity 112 in needle base 110. Second catch 108 catches needle base 110 such that when plunger 102 is retracted (pulled rearward), as shown in FIG. 4, second catch 108 pulls needle 106 into barrel 104. Second catch 108 and cavity 112 are configured to allow needle 106 to tilt off-axis, as shown in FIG. 4, after needle 106 is pulled entirely into barrel 104. The needle is tilted off-axis in that longitudinal central axis 107' of needle 106 when inside barrel 104 is not parallel to longitudinal central axis 107 of needle 106 before being pulled into barrel 104. To allow off axis-tilting, a portion of cavity 112 may be sized larger than a portion of second catch 108, as will be discussed further below. With off-axis tilting, needle tip 114 is out of alignment with forward barrel opening 116. If plunger 102 is somehow pushed forward, needle tip 114 will abut shoulder wall 118 of barrel 104 and be prevented from exiting forward barrel opening 116.

With a large pushing force on the plunger 102, it might be possible for needle 106 to pierce through shoulder wall 118. Thus, syringe 100 comprises an additional safety feature to prevent plunger 102 from being pushed forward after needle 106 is pulled entirely into barrel 104. As shown in FIG. 4, plunger 102 has first catch 120. First catch 120 may be a disk or flange on the top portion of plunger 120. After needle tip 114 is pulled into barrel 104, first catch 120 snaps into lock section 122 of barrel 104. After first catch 120 enters lock section 122, first catch 120 will abut first flat area 124 (FIG. 1B) of lock section 122 if plunger 102 is pushed forward. Abutment with first flat area 124 prevents plunger 102 from being pushed forward to an extent that would allow needle tip 114 to pierce shoulder wall 118 of barrel 104. First catch 120 will abut second flat area 126 (FIG. 1B) of lock section 122 if plunger 102 is pulled rearward. Abutment with second flat area 126 prevents plunger 102 from being retracted to an extent that would allow needle tip 114 to be pulled out of barrel 104.

Barrel 104 comprises features that allow for initial insertion of plunger 102 into barrel 104 during manufacturing and industrial assembly of the syringe. For example, rear segment 132 of barrel 104 may be tapered, as seen in FIG. 1B. The taper facilitates insertion of plunger 102 into rear barrel opening 144 at the rear of barrel 104 during industrial assembly. During industrial assembly, a specialized mechanical system may advance first catch 120 passed lock section 122 to a position in front of bevel 123 (above bevel 123 in the illustration of FIG. 1B), at which time plunger 102 is at a first position (position A in FIG. 2). To draw fluid, such as a therapeutic agent, into barrel cavity 105, plunger 102 is pushed to position A' and then pulled back to the first position. To inject the therapeutic agent into the patient, plunger 102 is pushed from the first position to a second position (position B in FIG. 3). Next, plunger 102 may be pulled from the second position to a third position (position C in FIG. 4). When plunger 102 is in the third position, first catch 120 is locked in lock section 122 by first flat area 124 and second flat area 126, as previously described.

Referring again to FIG. 1A, barrel 104 comprises barrel forward segment 128, barrel rear segment 132, and barrel medial segment 130 located between barrel forward segment 128 and barrel rear segment 132. Barrel forward segment 128 comprises the front tip of barrel 104, through which forward barrel opening 116 is formed. Barrel forward segment 128 comprises needle holder 127 of barrel 104, on which needle base 110 is removably attached. Barrel 104 comprises barrel interior surface 138, which extends from barrel forward segment 128 to barrel rear segment 132. Needle base 110 of needle 106 is configured for attachment on needle holder 127. Needle base 110 detaches from needle holder 127 when plunger 102 is moved from its second position (position B in FIG. 3) to its third position (position C in FIG. 4).

Referring again to FIG. 1B, barrel rear segment 132 has neck section 134, rear section 136, and lock section 122 between neck section 134 and rear section 136. Neck section 134 is adjacent to (connects to) barrel medial segment 130. Neck section 124 comprises bevel 123, which widens in diameter as it leads to barrel medial segment 130. Barrel interior surface 138 has lock section diameter 140 (first internal diameter) at lock section 122 and neck section diameter 142 (second internal diameter) at neck section 134. Neck section diameter 142 is less than lock section diameter 140.

Plunger 102 comprises first catch 120 (FIG. 2), as previously mentioned. Plunger 102 (comprising first catch 120) is sized to pass through rear barrel opening 144 (FIG. 1B) formed through rear section 136 during industrial assembly. After industrial assembly, plunger 102 is configured to move from the first position (position A in FIG. 2) at which first catch 120 is barrel medial segment 130, then to the second position (position B in FIG. 3) at which first catch 120 is in barrel forward segment 128, and then to the third position (position C in FIG. 4) at which first catch 120 is in lock section 122.

Plunger 102 comprises second catch 108 (FIG. 2), as previously mentioned. Second catch 108 is configured to attach to needle base 110 when plunger 102 is at the second position (position B in FIG. 3). When the user retracts plunger 102 partially out of barrel 104, second catch 108 pulls needle base 110 toward barrel rear segment 132, during which time plunger 102 is moved from the second position to the third position (position C in FIG. 4).

Figure 5A:
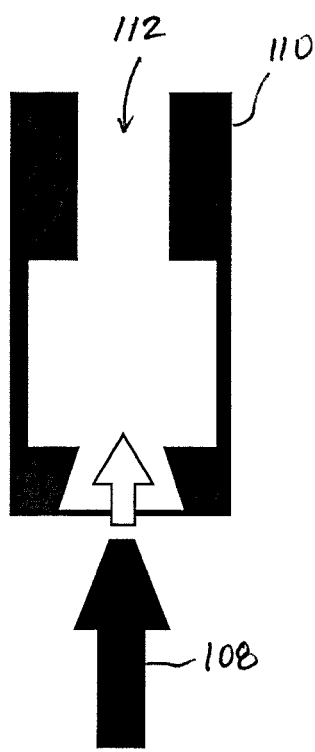
FIGS. 5A-5B are cross-section views showing the second catch of the plunger relative to the needle base.
Figure 5B:
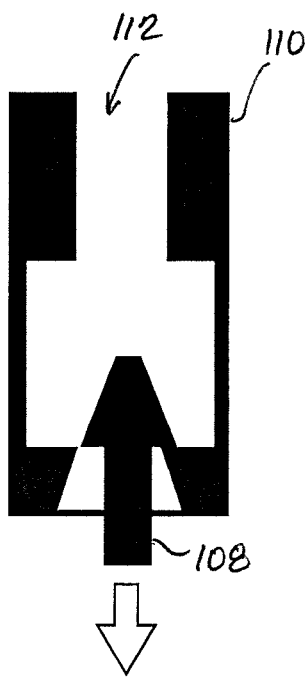
Figure 5C:
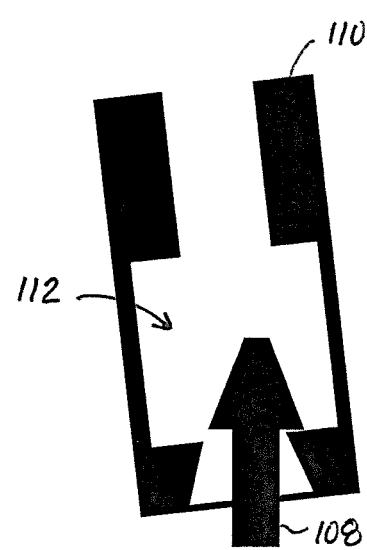
FIG. 5C is a cross-sectional view showing a relative orientation of the second catch of the plunger and the needle base.

FIG. 5A shows the relative positions of second catch 108 and needle base 110 when plunger 102 is at position A' in FIG. 2. Second catch 108 is in the form of a post. Second catch 108 comprises a shaft and a tapered barb, which is sized to squeeze into the entry opening of cavity 112 of needle base 110. FIG. 5B shows the relative positions of second catch 108 and needle base 110 when plunger 102 is at position B in FIG. 3. The tapered barb of second catch 108 has entered cavity 112 of needle base 110 and catches an edge of the entry opening of cavity 112. FIG. 5C shows the relative orientations of second catch 108 and needle base 110 when plunger 102 is at position C in FIG. 4. A portion of cavity 112 is sized larger than the tapered barb of second catch 108, which allows off axis-tilting of needle 106 as previously discussed.

Referring again to FIG. 4, needle 106 has longitudinal needle length Ln from needle tip 114 to needle base 110. Longitudinal needle length Ln runs along longitudinal central axis 107' of needle 106. A needle storage portion of barrel cavity 105 extends from shoulder wall 118 to first flat area 124. The needle storage portion of barrel cavity 105 has longitudinal length Lb that is greater than longitudinal length Ln. Longitudinal length Lb is parallel to central axis A of barrel medial segment 130.

Figure 6:
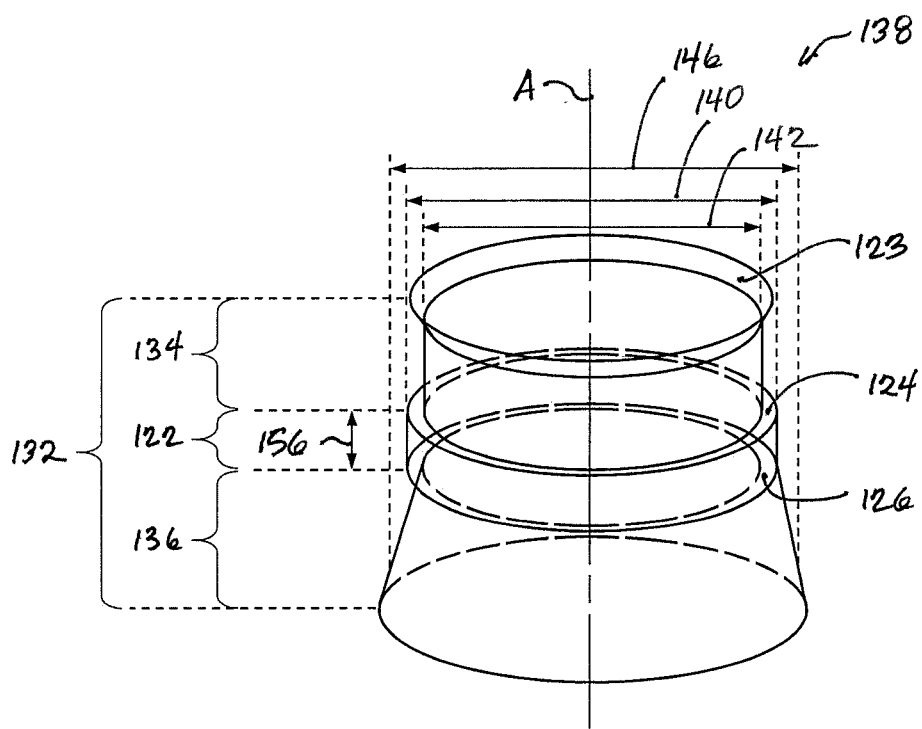
FIG. 6 is an axonometric view of a barrel interior surface at the rear segment of the barrel, showing the notch of the barrel.

Referring to FIGS. 1B and 6, barrel interior surface 138 has rear section diameter 146 (third internal diameter) at rear section 136 of barrel rear segment 132. Rear section diameter 146 is greater than lock section diameter 140 (first internal diameter). Rear section diameter 146 is greater than neck section diameter 142 (second internal diameter). As shown in FIG. 6, barrel interior surface 138 is frustoconical at rear section 136 of barrel rear segment 132. The frustoconical shape provides the taper, mentioned above, to facilitate initial insertion of plunger 102 into rear barrel opening 144 during industrial assembly. As seen in FIG. 1B, barrel interior surface 138 has medial segment diameter 148 (fourth internal diameter) at barrel medial segment 130. Medial segment diameter 148 is greater than or equal to lock section diameter 140.

Figure 7:
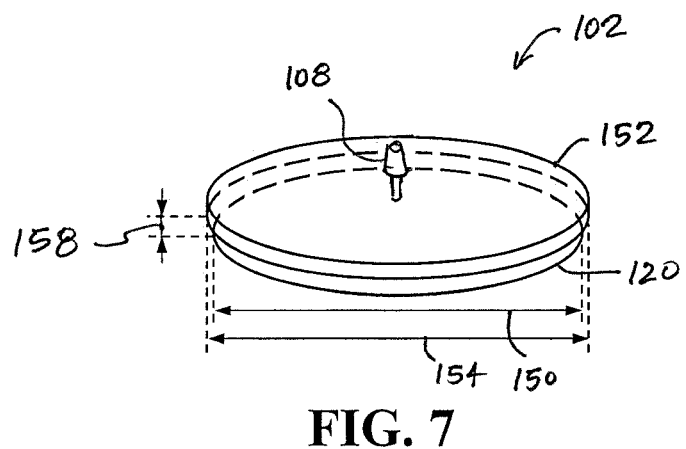
FIG. 7 is an axonometric view of the first catch, the second catch, and an elastic seal of the plunger.

FIG. 7 shows the top portion of plunger 102 before plunger 102 is installed into barrel 104 during manufacturing and industrial assembly. First catch 120 of plunger 102 is a disk having catch diameter 150 that is less than rear section diameter 146 (FIG. 6) at rear section 136 of barrel rear segment 132. Plunger 102 comprises an elastic seal 152 that is made of material that is more flexible than that of first catch 120. First catch 120 is made of material that is more rigid than that of elastic seal 152. Elastic seal 152 is configured to slide against barrel interior surface 138 as plunger 102 is moved from the first position (position A in FIG. 2) to the second position (position B in FIG. 3), and then to the third position (position C in FIG. 4). Elastic seal 152 enables plunger 102 to push any fluid contained in barrel cavity 105 out of forward barrel opening 116 when plunger is moved from the first position to the second position. Elastic seal 152 has seal diameter 154 that is greater than catch diameter 150 before plunger 102 is installed into barrel 104 during manufacturing and industrial assembly. After plunger 102 is installed into barrel 104, elastic seal 152 is compressed against barrel interior surface 138. After plunger 102 is installed into barrel 104, seal diameter 154 may be greater than or equal to catch diameter 150.

As mentioned above, first catch 120 comes to rest on bevel 123 (FIG. 6) when the user pulls plunger 102 from position A' to position A (first position) in FIG. 2. Bevel 123 functions as a ramp. Bevel 123 provides some resistance to further pulling of plunger 102. The resistance is overcome when the user applies additional pulling force on plunger 102. With the pulling additional force, first catch 120 passes through neck section 134 and becomes seated in lock section 122. When passing through neck section 134, first catch 120 may deform such that catch diameter 150 reduces in size and/or barrel 104 deforms such that neck section diameter 142 increases in size. The amount of pulling force used on plunger 102 through neck section 134 is insufficient to unseat first catch 120 from lock section 122. First surface area 124 and second surface area 126 at lock section 122 provide more resistance than bevel 123. When first catch 120 is in lock section 122, catch diameter 150 (FIG. 7) is equal to lock section diameter 140 (FIG. 6).

Referring FIGS. 1B, 6 and 7, lock section 122 of barrel rear segment 132 is a notch in barrel interior surface 138. The notch forms an indentation in barrel interior surface 138. The notch has notch height 156 (FIGS. 1B and 6) in a longitudinal direction and a notch depth that defines lock section diameter 140. First catch 120 has catch height 158 (FIG. 7) in the longitudinal direction. Notch height 156 is greater than or equal to catch height 158. Notch height 156 is defined by a separation distance between first flat area 124 of barrel interior surface 138 and second flat area 126 of barrel interior surface 138. First flat area 124 and second flat area 126 are perpendicular to the longitudinal direction. The longitudinal direction corresponds to central axis A (FIG. 4) of barrel medial segment 130. The perpendicular orientation helps to prevent first catch 120 from unseated from lock section 122.

From the forgoing description, it will be appreciated that syringe 100 is adapted to contain needle 106 in barrel 104 after injection and avoid potential or accidental needle penetration of barrel shoulder wall 118. This provides an additional layer of safety to the off-axis tilt of needle 106, which brings needle tip 114 out of alignment with forward barrel opening 116.

The locking mechanism, comprising first catch 120 and lock section 122 may, in non-limiting aspects, be integral parts of plunger 102 and barrel 104, respectively. Thus, the locking mechanism may be implemented without additional parts, thereby reducing production complexity and cost. In addition, syringe 100 allows for the use of different cannulas (e.g., needles) of different sizes and thus different clinical applications.

Another potential advantage of the barrel surface notch design of lock section 122 is ease of manufacture. A common manufacturing method for syringes is injection molding, where a male-female mold is used to produce the barrel. Slight modifications can be made to an existing male portion of the mold to enable automated production of the barrel surface notch design of lock section 122. By modifying an existing mold, a manufacturer may avoid having to purchase a new mold or to implement a secondary operation to form lock section 122 in the barrel.

While various forms of the invention have been illustrated and described, it will also be apparent that various modifications may be made without departing from the scope of the invention. It is also contemplated that various combinations or subcombinations of the specific features and aspects of the disclosed embodiments may be combined with or substituted for one another in order to form varying modes of the invention. Accordingly, it is not intended that the invention be limited, except as by the appended claims.

What is claimed is:

1. A syringe comprising:
    a barrel comprising a barrel forward segment, a barrel rear segment, a barrel medial segment between the barrel forward segment and the barrel rear segment, and a barrel interior surface extending from the barrel rear segment to the barrel forward segment, the barrel rear segment having a neck section adjacent the barrel medial segment, a rear section, and a lock section between the neck section and the rear section, the barrel interior surface having a first internal diameter at the lock section and a second internal diameter at the neck section, the second internal diameter being less than the first internal diameter;
    a needle configured for attachment on the barrel forward segment;
    a plunger comprising a first catch, the plunger sized to pass through an opening formed through the rear section of the barrel rear segment, the plunger configured to be pushed from a first position at which the first catch is in the barrel medial segment, then to a second positon at which the first catch is in the barrel forward segment, and then pulled to a third positon at which the first catch is in the lock section of the barrel rear segment, and
    wherein the needle comprises a needle tip and a needle base that defines a cavity,
    wherein the needle base is a continuous portion of the needle,
    wherein the needle base comprises an edge located inside the cavity,
    wherein the plunger comprises a second catch, wherein the second catch comprises a shaft and a tapered barb, and wherein the second catch is configured to attach to the needle base by catching the edge of the needle base with the barb when the plunger is at the second position, and
    wherein the second catch is configured to pull the needle base at the edge toward the barrel rear segment when the plunger is moved from the second position to the third position.

2. The syringe of claim 1, wherein the needle has a longitudinal needle length from the needle tip to the needle base, and the barrel medial segment has a longitudinal length that is greater than the longitudinal needle length.

3. The syringe of claim 1, wherein the plunger comprises an elastic seal made of material that is more flexible than that of the first catch, and the elastic seal is configured to slide against the barrel interior surface as the plunger is moved from the first position to the second position and then to the third position.

4. The syringe of claim 1, wherein the barrel interior surface has a third internal diameter at the rear section of the barrel rear segment, and the third internal diameter is greater than the first internal diameter.

5. The syringe of claim 4, wherein the first catch has a catch diameter less than the third internal diameter.

6. The syringe of claim 1, wherein the barrel interior surface is frustoconical at the rear section of the barrel rear segment.

7. The syringe of claim 1, wherein the lock section of the barrel rear segment is a notch in the barrel interior surface.

8. The syringe of claim 7, wherein the notch has a notch height in a longitudinal direction and a notch depth that defines the first internal diameter, the first catch has catch height in the longitudinal direction, and the catch height is less than or equal to the notch height.

9. The syringe of claim 8, wherein the notch height is defined by a separation distance between a first flat area of the barrel interior surface and a second flat area of the barrel interior surface.

10. The syringe of claim 9, wherein the first flat area and the second flat area are perpendicular to the longitudinal direction.

\* \* \* \* \*